United States Patent [19]

Gries

[11] Patent Number: 4,996,368

[45] Date of Patent: Feb. 26, 1991

[54] PROCESS FOR THE PURIFICATION AND STABILIZATION OF PERFLUOROPOLYETHERS

[75] Inventor: Thomas Gries, Frankfurt am Main, Fed. Rep. of Germany

[73] Assignee: Hoechst Aktiengesellschaft, Frankfurt am Main, Fed. Rep. of Germany

[21] Appl. No.: 471,867

[22] Filed: Jan. 29, 1990

[30] Foreign Application Priority Data

Jan. 31, 1989 [DE] Fed. Rep. of Germany ....... 3902803

[51] Int. Cl.$^5$ .............................................. C07C 41/34
[52] U.S. Cl. .................................... 568/601; 568/615; 568/621; 568/677; 568/699; 568/581; 568/604; 252/77; 252/78.1; 252/67
[58] Field of Search ............... 568/615, 601, 621, 677, 568/581, 699; 252/77, 67, 78.1

[56] References Cited

U.S. PATENT DOCUMENTS 3,665,041 5/1972 Sianesi et al. .
3,985,810 10/1976 Von Halasz et al. .

FOREIGN PATENT DOCUMENTS 0158446 10/1985 European Pat. Off. .

*Primary Examiner*—Howard T. Mars

[57] ABSTRACT

The invention relates to a process for the stabilization and purification of perfluoropolyethers of the general formulae (I) or (II)

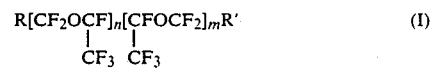

in which
$R = -F$ or $-C_aF_{2a+1}$
$R' = -F$ or $-C_bF_{2b+1}$
n,m = 0,1, ... or 12, n being identical with or different from m, $1 \leq n+m \leq 15$
a,b = 1,2, ... or 10, a being identical with or different from b

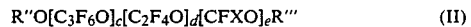

in which
$R'' = -C_fF_{2f+1}$
$R''' = -C_gF_{2g+1}$
$X = -F$ or $-CF_3$
c,d,e = integers such that the molecular weight of the perfluoropolyether is between 200 and 2000, where c, d and e may be identical or different and the units $[C_3F_6O]_c$, $[C_2F_4O]_d$, and $[CFXO]_e$ may be randomly distributed along the molecular chain of the perfluoropolyether, or of mixtures of perfluoropolyethers of this type. The process comprises heating the perfluoropolyethers or mixtures thereof to 150°–360° C. in the presence of a catalyst which contains one or more elements from groups IA, IIA, IIIA, IVA or IVB or compounds thereof.

11 Claims, No Drawings

PROCESS FOR THE PURIFICATION AND STABILIZATION OF PERFLUOROPOLYETHERS

The invention relates to a process for the stabilization and purification of perfluoropolyethers of the general formulae (I) or (II)

$$R[CF_2OCF]_n[CFOCF_2]_mR' \quad (I)$$
$$\phantom{R[CF_2OCF]_n}|\phantom{[CFOCF_2]}|$$
$$\phantom{R[CF_2OCF]_n}CF_3\phantom{FOC}CF_3$$

in which
R = —F or —$C_aF_{2a+1}$
R' = —F or —$C_bF_{2b+1}$
n,m = 0,1, ... or 12, n being identical with or different from m, $1 \leq n+m \leq 15$
a,b = 1,2, ... or 10, a being identical with or different from b $$R''O[C_3F_6O]_c[C_2F_4O]_d[CFXO]_eR''' \quad (II)$$

in which
R'' = —$C_fF_{2f+1}$
R''' = —$C_gF_{2g+1}$
X = —F or —$CF_3$
c,d,e = integers such that the molecular weight of the perfluoropolyether is between 200 and 2000, where c, d and e may be identical or different and the units $[C_3F_6O]_c$, $[C_2F_4O]_d$, and $[CFXO]_e$ may be randomly distributed along the molecular chain of the perfluoropolyether, or of mixtures of perfluoropolyethers of this type.

The preparation of these perfluoropolyethers has been disclosed in U.S. Pat. No. 3,665,041, U.S. Pat. No. 3,985,810 and JP-A258/103,334 (Application number Sho 56/199,999). Depending on the type and method of preparation, perfluoropolyethers contain different amounts of various byproducts, which even in trace amounts of 0.1% by weight impair the inert character and the application of the perfluoropolyethers —these being neutral and stable in pure form—due to subsequent oxidation, i.e. the slow evolution of acidic and corrosive gases, and due to an unpleasant odor.

These byproducts are generally toxic or reactive fluorinated compounds which may additionally contain hydrogen, and under the conditions of use of perfluoropolyethers they also form toxic or reactive acidic products of relatively low molecular weight, such as for example carbonyl fluorides, perfluorinated carboxylic acids, fluoroalkenes or hydrogen fluoride.

The important use of the perfluoropolyethers as liquid phase heat transfer media or vapor phase heat transfer media (for example in the condensation soldering of electronic components described in U.S. Pat. No. 3,866,307, U.S. Pat. No. 3,904,102 and U.S. Pat. No. 4,721,578) or as a test liquid for testing electronic components (for example the thermal shock test, gross leak test and burn in test as described in EP-A-No. 0,203,348) requires that the abovementioned impurities should be absent 1. in order to obtain compatibility of components and equipment with the materials,
2. in order to avoid danger to the user and to the environment from toxic products and
3. in order to permit use over a long period.

It is therefore desirable to find an effective and economical industrial purification method in order to be able to convert perfluoropolyethers into a truly inert form which satisfies these criteria.

An example of the purification of certain perfluoropolyethers is described in EP-B-No. 0,158,446. However, this process is limited to perfluoropolyethers which can be degassed at 150°-200° C. without themselves being evaporated. The latter process moreover requires radiation with UV light and the industrially complex handling of aggressive or expensive gases such as fluorine, chlorine or oxygen.

The working up of perfluoropolyethers by drying and distillation, which is described in JP-No. A2-58/103,334 (see above), does not produce pure products, as is shown by the hydrogen analyses quoted therein, and leads to the formation of fluorinated carboxylic acids and hydrogen fluoride.

Surprisingly, it has now been found that the perfluoropolyethers of the formulae (I) and (II) defined above, prepared for example according to Sho 58/103,334 can be purified by thermally decomposing the byproducts at high temperatures with the aid of a catalyst.

The invention relates to a process for the stabilization and purification of perfluoropolyethers of the general formulae (I) or (II)

$$R[CF_2OCF]_n[CFOCF_2]_mR' \quad (I)$$
$$\phantom{R[CF_2OCF]_n}|\phantom{[CFOCF_2]}|$$
$$\phantom{R[CF_2OCF]_n}CF_3\phantom{FOC}CF_3$$

in which
R = —F or —$C_aF_{2a+1}$
R' = —F or —$C_bF_{2b+1}$
n,m = 0,1, ... or 12, n being identical with or different from m, $1 \leq n+m \leq 15$
a,b = 1,2, ... or 10, a being identical with or different from b $$R''O[C_3F_6O]_c[C_2F_4O]_d[CFXO]_eR''' \quad (II)$$

in which
R'' = —$C_fF_{2f+1}$
R''' = —$C_gF_{2g+1}$
X = —F or —$CF_3$
c,d,e = integers such that the molecular weight of the perfluoropolyether is between 200 and 2000, where c, d and e may be identical or different and the units $[C_3F_6O]_c$, $[C_2F_4O]_d$, and $[CFXO]_e$ may be randomly distributed along the molecular chain of the perfluoropolyether, or of mixtures of perfluoropolyethers of this type, which comprises heating the perfluoropolyethers or mixtures thereof to 150°-360° C. in the presence of a catalyst which contains one or more elements of the groups IA, IIA, IIIA, IVA or IVB of the periodic table or compounds thereof.

Particularly important perfluoropolyethers are those of the formula (I) which have one of the feature combinations 1 to 3:
R = R' = —$C_2F_5$
n = 1,2,3 or 4; m = 0,1,2,3 or 4
n being identical with or different from m
R = —$C_2F_5$, R' = —$C_7F_{15}$
n = 1,2,3 or 4; m = 0
R = —$C_2F_5$, R' = —F
n = 1,2 ... or 9; m = 0

Other important perfluoropolyethers are those of the formula (II) which have one of the feature combinations 4 to 7:

R″=R‴=—CF₃; X=—F
c=0; d,e≠0
R″=R‴=—CF₃; —C₂F₅ or —C₃F₇
X=—F or —CF₃
c, e≠0; d=0
R″=—C₃F₇ or —C₄F₉
R‴=—C₂F₅ or —C₃F₇
c=e=0; d≠0
R″=—CF₃, —C₂F₅ or —C₃F₇
R‴=—CF₃, —C₂F₅ or —C₃F₇
c≠0; d=e=0

The process according to the invention can be used to purify and stabilize any desired mixtures of a plurality of perfluoropolyethers of the formulae (I) or (II), but a particularly important embodiment is the purification and stabilization of a single ether, in particular an ether of the formula (I) having one of the feature combinations 1., 2. or 3. A further particularly important embodiment is the purification and stabilization of a 3-component mixture containing a symmetrical ether of the formula

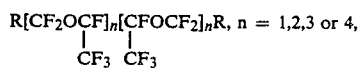
R[CF₂OCF]ₙ[CFOCF₂]ₙR, n = 1,2,3 or 4,
    |           |
    CF₃      CF₃ another symmetrical ether of the formula

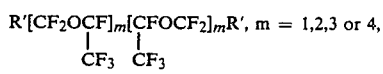
R′[CF₂OCF]ₘ[CFOCF₂]ₘR′, m = 1,2,3 or 4,
    |           |
    CF₃      CF₃ where m≠n, and the corresponding asymmetrical ether of the formula

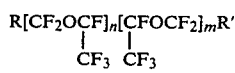
R[CF₂OCF]ₙ[CFOCF₂]ₘR′
    |           |
    CF₃      CF₃ where R and R′ again have the general definitions given above (R being identical with or different from R′).

3-Component mixtures of this type are prepared by electrolytic decarboxylation of a mixture of two perfluorocarboxylic acids of the formulae

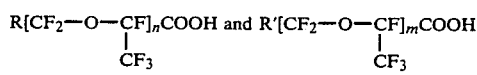
R[CF₂—O—CF]ₙCOOH and R′[CF₂—O—CF]ₘCOOH
         |                        |
         CF₃                    CF₃

(cf. JP-A-2 Sho 58/103,334).

A further particularly important embodiment is the purification and stabilization of a 2-component mixture containing a symmetrical ether of the formula R[]ₙ[]ₙR and an asymmetrical ether of the formula R[]ₙR′, where n=1,2,3 or 4 and [] represents

[CF₂OCF].
    |
    CF₃

The perfluoropolyethers or mixtures thereof are preferably heated to 200°–360° C., in particular to 270°–330° C.

The catalysts used are substances which contain one or more elements from the groups IA (Li to Cs), IIA (Be to Ba), IIIA (B to Tl), IVA (C to Pb) or IVB (Ti to Hf) or compounds thereof. Examples of suitable compounds are the oxides, carbonates, halides and hydroxides. The catalysts preferably contain Na, K, Cs, Mg, Ca, Ba, Ti, B, Al, C or Si. Particularly suitable catalysts are activated carbon, calcium oxide, titanium dioxide, potassium fluoride and aluminum oxide.

The process according to the invention can in principle be carried out in the liquid phase in a simple stirred vessel or by passing the liquid over a fixed-bed catalyst. However, it is advantageous to evaporate the perfluoropolyethers which are to be purified and to pass them in gaseous form over a fixed-bed catalyst in a tube reactor, i.e. to carry out the thermolysis of the impurities as a gas/solid reaction. In the case of high-boiling perfluoropolyethers, evaporation can be achieved by heating in vacuo. In the thermolysis, it is not critical in which spatial arrangement the reaction takes place. Preferably however, the gaseous perfluoropolyether is passed upwards through a vertical tube reactor. The gaseous reaction products leave the reactor at the top and are then condensed.

The perfluoropolyethers purified according to the invention are thermally stable and do not release decomposition products in use. For applications in which a particularly high degree of purity is required, the said perfluoropolyethers can be obtained at a uniform purity of 99.9% (GC) by following the process according to the invention with customary separation processes, for example by scrubbing with water or aqueous solutions of alkali metal hydroxides or alkaline earth metal hydroxides, or by adsorption onto solids (for example with alkali metal hydroxides or alkaline earth metal hydroxides or alkali metal carbonates or alkaline earth metal carbonates, activated carbon, silica gel or Al₂O₃), optionally supplemented by a subsequent distillation.

In the case of gas phase operation where it is intended to perform an additional purification after the process according to the invention, it is advantageous to condense the gaseous reaction products leaving the top of the reactor in aqueous solutions of KOH or NaOH, the purified perfluoropolyethers separating out as a heavy phase at the bottom. Continuous operation is possible in this way. However, it is also possible to use a bubble column or a loop-type bubble column.

The products which have been purified by this process are stable, even in the presence of metals and of materials which are used in soldering electronic components, even for a period of 1000 hours at the boiling point. Even at temperatures of 350° C. (for example due to overheating) and in the presence of the above materials, the perfluoropolyethers are stable and do not form any toxic decomposition products. It is particularly noteworthy that the perfluoropolyethers which have been purified by the process according to the invention, in contrast to those which have not been purified by this method, do not form any perfluoroisobutene under thermal stress, perfluoroisobutene being a particularly toxic decomposition product which impairs the use of the perfluoropolyethers. The purification according to the invention results in a significant reduction of the solvent power of the perfluoropolyethers for the solder paste flux used when condensation soldering electronic components. The perfluoropolyethers stabilized according to the invention satisfy the criteria originally stated and are suitable in particular for us in condensation soldering.

The process according to the invention is also suitable for working up already used and hence contaminated perfluoropolyethers.

The percentages given in the following examples are percentages by weight unless otherwise stated or unless this is evident from the context.

COMPARISON EXAMPLE 4109 g of a crude product of 1=

$$(C_2F_5(CF_2OCF))_2$$
$$\phantom{(C_2F_5(CF_2O}|}$$
$$\phantom{(C_2F_5(CF_2OC}CF_3$$

(purity 86.5%), prepared by Kolbe-electrolysis of $$C_2F_5(CF_2OCF)_2COOH,$$
$$\phantom{C_2F_5(CF_2O}|}$$
$$\phantom{C_2F_5(CF_2OC}CF_3$$

were stirred for 5 h with 800 ml of 2.7% sodium hydroxide solution. After separation and washing with water, 3880 g were obtained. Vacuum distillation in a packed column 1.8 m in length with 50 theoretical plates at a reflux ratio of 20:1 gave a yield of 2235 g of 1 at a purity of at most 99.8% (GC). The material had a pH of 1 and reacted corrosively.

EXAMPLE 1

359 g of 2=

$$(C_2F_5(CF_2OCF)_3)_2,$$
$$\phantom{(C_2F_5(CF_2OC}|}$$
$$\phantom{(C_2F_5(CF_2OC}CF_3$$

with a pH of 1 were stirred for 20 h at 200° C. with 3.6 g of activated carbon. After filtering off the solid, it was washed with 10% strength sodium hydroxide solution. The pH was then neutral and the material did not liberate any acidic gases even when heated to 300° C.

Yield: 294 g.

EXAMPLE 2

807 g of crude product 1 were pumped for 1.5 h at 280° C. through a horizontally constructed earthenware pipe which was filled with 200 g of activated carbon, and then collected in a NaOH scrubber. Subsequent washing with water gave 604 g of purified 1 which will no longer oxidize.

EXAMPLE 3

2410 g of crude product 1 (purity 90.9%; 7.2% of $$C_2F_5(CF_2OCF)_2OCH_3 = \underline{3,} \text{ and}$$
$$\phantom{C_2F_5(CF_2O}|}$$
$$\phantom{C_2F_5(CF_2O}CF_3$$

$$1.5\% \text{ of } C_2F_5(CF_2OCF)_2COOCH_3 = \underline{4}),$$
$$\phantom{1.5\% \text{ of } C_2F_5(CF_2O}|}$$
$$\phantom{1.5\% \text{ of } C_2F_5(CF_2OC}CF_3$$

were passed in gaseous form at 320° C. through a heated steel pipe filled with activated carbon and collected in NaOH solution.

Subsequent washing with water gave 2151 g of 1. The substances 3 and 4 were completely removed. The sample did not show any signs of oxidation even after several days. Yield: 97%.

EXAMPLE 4

2337 g of 1 containing 3.5% of 3 were passed for 4.5 h at 305° C. in the gaseous phase through a heated steel pipe 1 m in length containing the activated carbon already used in Example 3 and condensed in a NaOH scrubber. After separation and washing with water, 2050 g of 1 were collected. GC analysis showed that was no longer present in the product. Subsequent vacuum distillation gave 1990 g of 1 having a purity greater than 99.9% (GC).

Yield: 88.3%

EXAMPLE 5

470 g of acidic crude product $$(C_2F_5(CF_2OCF)_4)_2$$
$$\phantom{(C_2F_5(CF_2OC}|}$$
$$\phantom{(C_2F_5(CF_2OC}CF_3$$

=5 were pumped in the liquid phase at 300° C. through a heated pipe 25 cm in length containing 8.4 g of a 1:3 mixture (ratio by weight) of potassium fluoride and activated carbon. After washing with KOH solution, 365 g of 5 were obtained having a boiling point of 102° C. at 1 mbar. The pH was neutral.

EXAMPLE 6

Various catalysts were used, at 280° to 350° C. in a tube reactor 25 cm in length, for purifying and stabilizing a crude product of the composition $$(C_3F_7OCF)_2 \phantom{xx} = \mathbf{6} \phantom{xx} 97.2\%$$
$$\phantom{(C_3F_7OC}|}$$
$$\phantom{(C_3F_7OC}CF_3$$

$$C_3F_7OCF-COOCH_3 \phantom{xx} = \mathbf{7} \phantom{xx} 0.8\%$$
$$\phantom{C_3F_7OC}|}$$
$$\phantom{C_3F_7OC}CF_3$$

$$C_3F_7OCF-OCH_3 \phantom{xx} = \mathbf{8} \phantom{xx} 1.4\%$$
$$\phantom{C_3F_7OC}|}$$
$$\phantom{C_3F_7OC}CF_3$$

The results were as follows:

| Catalyst | Throughput g/h | Mass of starting material Mass of catalyst | Final content (% GC) of 7 | 8 |
|---|---|---|---|---|
| Activated carbon | 20 | 9 | — | 0.01 |
| KF/activated carbon | 21 | 12.9 | — | — |
| Silica gel | 22 | 8.0 | — | 0.04 |
| Aluminum oxide | 18 | 6.9 | — | — |
| Aluminum oxide | 9 | 62.6 | — | — |
| KF/aluminum oxide | 24 | 6.1 | — | — |
| 4 Å molecular sieve | 18 | 5.4 | 0.02 | 0.02 |
| TiO$_2$/activated carbon | 18 | 8.6 | — | 0.03 |
| Calcium carbonate | 17 | 7.7 | — | 0.02 |

EXAMPLE 7

177 g of an acidic crude mixture of perfluoropolyethers (46% of $$C_3F_7OCF-(CFOCF_2)_3C_2F_5$$
$$\phantom{C_3F_7OC}|\phantom{-(CFOC}|$$
$$\phantom{C_3F_7OC}CF_3\phantom{-(CF}CF_3$$

=9, 20% of 6 and 27% of

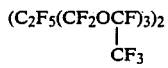

=10 were passed at 340° C. through a steel reactor (length=25 cm; diameter=1 cm) with 3.4 g of activated carbon and then washed with KOH solution. The material did not subsequently oxidize and its pH was neutral.

EXAMPLE 8

126 g of 6 containing 1% of 8, 3% of 7 and 4% of

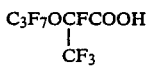

=11 were passed at 300° C. for 13 h through a steel pipe filled with 15 g of aluminum oxide. After condensation, 7, 8 and 11 had been completely removed.

EXAMPLE 9

After evaporating, 357 kg of 1, containing 1.0% of 4 and 4.1% of 3 were passed at 250° to 300° C. for 370 h through a heated steel pipe 1 m in length which was filled with 1.2 kg of aluminum oxide and condensed in a KOH scrubber. In this process, 3 and 4 were selectively decomposed so that their content in the purified product was below 0.1%.

EXAMPLE 10

The solubility of a flux for solder pastes, which is used in condensation soldering of electronic components was investigated in each case at 20° and 220° C. a) in a crude product of 1 and b) in 1 which had been purified by thermolysis in the gaseous phase in the presence of an $Al_2O_3$ catalyst and subsequently scrubbed with aqueous NaOH solution. Determination of the solubility of the flux was carried out using gas chromatography after silylation of the samples. A standardized solution of the flux in trichlorotrifluoroethane was used as reference sample.
A. 40 g of crude product 1 were stirred for 3 h at 20° C. with 0.4 g of flux and then filtered.
B. 40 g of crude product 1 were boiled under reflux for 3 h at 220° C. with 0.4 g of flux and then filtered.
C. 40 g of purified 1 were stirred for 3 h at 20° C. with 0.4 g of flux and then filtered.
D. 40 g of purified 1 were boiled under reflux for 3 h at 220° C. with 0.4 g of flux and then filtered.
Result: The flux content was as follows:
A: 0.3%
B: 0.3%
C: 0.1%
D: 0.1%

EXAMPLE 11

Four 100 ml glass ampoules were each filled with 20 ml of 1 which had been previously purified and stabilized as in Example 10, but using KF/activated carbon instead of $Al_2O_3$. 2.5 g of solder paste were added to three samples the paste being as used in condensation soldering. Two samples additionally contained a piece of V4A sheet steel. The sealed ampoules were kept at 220° C. for 1000 h.
After cooling to −78° C. the ampoules were cut open at the top and sealed again using a septum screw fitting. After heating the ampoules, samples were taken from the gas space using a gas-tight syringe and examined by gas chromatography. In addition to an overall gas chromatogram, the content of perfluoroisobutene was determined quantitatively.
Result: None of the samples revealed the presence of decomposition products of 1. None of the samples contained perfluoroisobutene (detection limit 0.1 ppm).

EXAMPLE 12

Four glass ampoules were filled with 1, solder paste and a piece of sheet steel as described in Example 11. The samples were then kept at 350° C. for 100 h. Working up and analysis of the samples was carried out described in Example 11.
Result: None of the samples revealed the presence of decomposition products of 1. None of the samples contained perfluoroisobutene.

I claim:
1. A process for the stabilization and purification of a perfluoropolyether of the general formulae (I) or (II)

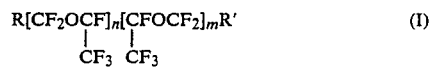

in which
R=—F or —$C_aF_{2a+1}$
R'=—F or —$C_bF_{2b+1}$
n,m=0,1, ... or 12, n being identical with or different from m, $1 \leq n+m \leq 15$
a,b=1,2, ... or 10, a being identical with or different from b

in which
R''=—$C_fF_{2f+1}$
R'''=—$C_gF_{2g+1}$
X=—F or —$CF_3$
c,d,e=integers such that the molecular weight of the perfluoropolyether is between 200 and 2000, where c, d and e may be identical or different and the units $[C_3F_6O]_c$, $[C_2F_4O]_d$, and $[CFXO]_8$ may be randomly distributed along the molecular chain of the perfluoropolyether,
or of mixtures of perfluoropolyethers of this type, which comprises heating the perfluoropol-yether or mixtures thereof to 150°–360° C. in the presence of a catalyst which contains one or more elements of the groups IA, IIA, IIIA, IVA or IVB of the periodic table or compounds thereof.
2. The process as claimed in claim 1, wherein a perfluoropolyether of the formula (I) is used in which R=R'=—$C_2F_5$, n=1,2,3 or 4 and m=0,1,2,3 or 4 and n may be identical to or different from m.
3. The process as claimed in claim 1, wherein a perfluoropolyether of the formula (I) is used in which R=—$C_2F_5$, R'=—$C_7F_{15}$, n=1,2,3 or 4 and m=0.
4. The process as claimed in claim 1, wherein a perfluoropolyether of the formula (I) is used in which R=—$C_2F_5$, R'=—F, n=1,2, ... 8 or 9 and m=0.
5. The process as claimed in claim 1, wherein a perfluoropolyether of the formula (II) is used which has one of the feature combinations A, B, C or D
R''=R'''=—$CF_3$; X=—F
c=0; d,e≠0

R″=R‴=—CF₃; —C₂F₅ or —C₃F₇
X=—F or —CF₃
c,e≠0; d=0
R″=—C₃F₇ or —C₄F₉
R‴=—C₂F₅ or —C₃F₇
c=e=0; d≠0
R″=—CF₃, —C₂F₅ or —C₃F₇
R‴=—CF₃, —C₂F₅ or —C₃F₇
c≠0; d=e=0

6. The process as claimed in claim 1, wherein a mixture of three perfluoropolyethers is used containing a symmetrical ether of the formula

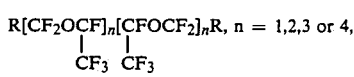, n = 1,2,3 or 4, another symmetrical ether of the formula

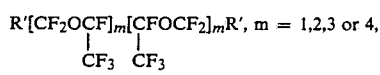, m = 1,2,3 or 4, where m≠n, and the corresponding asymmetrical ether of the formula

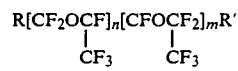

7. The process as claimed in claim 1, wherein a mixture of two perfluoropolyethers is used containing a symmetrical ether of the formula

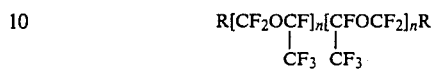

and an asymmetrical ether of the formula

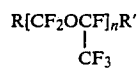

where n=1,2,3 or 4.

8. The process as claimed in claim 1, wherein the system is heated to 200° to 360° C.

9. The process as claimed in claim 1, wherein the system is heated to 270° to 330° C.

10. The process as claimed in claim 1, wherein a catalyst is used which contains one or more of the elements Na, K, Cs, Mg, Ca, Ba, Ti, B, Al, C or Si.

11. The process as claimed in claim 1, wherein the perfluoropolyether is passed in gaseous form over the catalyst.

* * * * *